US00PP15143P2

(12) United States Plant Patent
Bradford

(10) Patent No.: US PP15,143 P2
(45) Date of Patent: Sep. 14, 2004

(54) NECTARINE TREE NAMED 'AUGUST BRIGHT'

(50) Latin Name: *Prunus persica*
Varietal Denomination: August Bright

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 116 days.

(21) Appl. No.: 10/302,978

(22) Filed: Nov. 25, 2002

(51) Int. Cl.[7] ..... A01H 5/00
(52) U.S. Cl. ..... Plt./190
(58) Field of Search ..... Plt./190

(56) References Cited

U.S. PATENT DOCUMENTS

PP6,363 P 11/1988 Bradford

PP7,066 P 12/1989 Bradford

*Primary Examiner*—Anne Marie Grunberg

(57) ABSTRACT

The present invention relates to a nectarine tree, *Prunus persica*, and more particularly to a new and distinct variety broadly characterized by a medium size, vigorous, hardy, self-fertile, productive and regular bearing tree. The fruit matures under the ecological conditions described in mid August, with first picking on Aug. 12, 2002. The fruit is uniformly large in size, sweet and acidic in flavor, globose in shape, clingstone in type, firm in texture, yellow in flesh color, and mostly red in skin color. The variety was developed as a first generation cross using 'August Red' (U.S. Plant Pat. No. 6,363) nectarine as the selected seed parent and 'Diamond Princess' (U.S. Plant Pat. No. 7,066) peach as the selected pollen parent.

1 Drawing Sheet

Botanical classification: *Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'August Bright'. The present variety was hybridized by me in 1989, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'August Red' (U.S. Plant Pat. No. 6,363) nectarine as the selected seed parent and 'Diamond Princess' (U.S. Plant Pat. No. 7,066) peach as the selected pollen parent. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected pollen parent, 'Diamond Princess' (U.S. Plant Pat. No. 7,066) peach, by producing fruit that is yellow in flesh color and nearly full red in skin color, but is quite distinguished therefrom by producing fruit that is nectarine instead of peach, that is clingstone instead of freestone, and that matures about thirty-five days later.

The present variety is most similar to its selected seed parent, 'August Red' (U.S. Plant Pat. No. 6,363) nectarine, by producing nectarines that are nearly globose in shape, very firm in texture, clingstone in type, mostly red in skin color, and yellow with some red streaking in flesh color, but is distinguished therefrom by producing fruit that matures about two weeks earlier and that has a sweet kernel instead of bitter.

SUMMARY OF VARIETY

In summary, the present variety is characterized by a medium size, vigorous, hardy, self-fertile, productive and regular bearing tree. The fruit matures under the ecological conditions described in mid August, with first picking on Aug. 12, 2002. The fruit is uniformly large in size, sweet and acidic in flavor, globose in shape, clingstone in type, firm in texture, yellow in flesh color, and mostly red in skin color.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Aug. 15, 2002, on a six year old tree budded on 'Nemagard' (unpatented) rootstock. All major color code designations are by reference to the Inter-Society Color Council, National Bureau of Standards. Common color names are also used occasionally.

Tree

Size: Medium, reaching a height of 11' [3.35 m.] and a spread of 9' [2.74 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Medium, reaching a maximum diameter of 4¼" [108 mm.] after the sixth growing season.

*Texture.*—Shaggy.

*Bark color.*—Dark grayish yellowish brown [81. d.gy.yBr].

*Lenticels.*—Approximate number per square inch: 12. Color: Light yellowish brown [76. l.yBr]. Average Size: 5/16" [7.9 mm.].

Branches

*Size.*—Diameter of limb is 1⅞" [48 mm.] measured 12" above the crotch, typical of *Prunus persica*, and dependent upon cultural practices and climatic conditions.

*Texture.*—Smooth on 1st year wood, increasing roughness with age.

*Color.*—1st Year Wood Topside: Grayish red [19. gy.R]. 1st Year Wood Underside: Brilliant yellow green [116. brill.YG]. Older Wood: Dark yellowish brown [78. d.yBr].

*Lenticels.*—Approximate Number Per Square Inch: 48. Color: Light orange yellow [70. l.OY]. Typical size: 1/32" to 3/16" [0.8–4.8 mm.].

Leaves:

*Size.*—Large. Average Length: 6" [152 mm.]. Average Width: 1⅝" [41 mm.].

*Arrangement.*—Alternate.

*Thickness.*—Medium.

*Form.*—Elliptical.

*Apex.*—Acuminate.

*Base.*—Rounded to acute, with an average base angle of 90 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ½" [12.7 mm.]. Average Thickness: 1/16" [1.6 mm.]. Color: Brilliant yellow green [116. brill.YG].

*Stipules.*—Number: Occasionally 2 per leaf, no more than 6 per growing tip. Average Length: 5/16" [7.9 mm.]. Color: Brilliant yellow green [116. brill.YG] becoming Dark grayish reddish brown [47. d.gy.rBr] when old and dry.

*Glands.*—Number: 2 to 6. Position: Alternate, usually 2 on the petiole with the remainder on the base of blade. Size: Medium. Form: Mostly reniform, but some look globose while juvenile and take on reniform appearance with maturity. Color: Brilliant yellow green [116. brill.YG] becoming Moderate reddish brown [43. m.rBr] toward the center with age.

*Leaf buds.*—Conic.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Strong purplish pink [247. s.pPk].

Flowers: Perfect, complete, perigynous, usually a single pistil, typically thirty or more stamens, five sepals and petal locations alternately positioned.

*Type.*—Non-showy, small.

*Average flower diameter.*—1" [25.4 mm.].

*Number of petals.*—Almost always five.

*Petal shape.*—Oval to somewhat heart shaped.

*Petal margin.*—Very wavy.

*Average petal diameter.*—½" [12.7 mm.].

*Average petal length.*—⅝" [15.9 mm.].

*Petal apex.*—Rounded with a small notch located at the top center of the margin on many.

*Petal base.*—Rounded.

*Petal color.*—Pale pink [7. p.Pk] toward the apex and margin blending to Moderate purplish pink [250. m.pPk] toward the base.

*Anther color.*—Dark red [16. d.R] over a Brilliant orange yellow [67. brill.OY] center.

*Stigma color.*—Light greenish yellow [101. l.gY].

*Sepal color.*—Grayish purplish red [262. gy.pR].

*Sepal length.*—9/32" [7 mm.].

*Sepal width.*—3/16" [5 mm.].

*Average pistil length.*—¾" [19.1 mm.].

*Average stamen length.*—9/16" [14.3 mm.].

*Fragrance.*—Moderate when nectar is present.

*Blooming period.*—A few days later than average compared with other varieties.

*Onset of bloom.*—One percent on Mar. 5, 2002.

*Date of full bloom.*—Mar. 15, 2002.

*Duration of bloom.*—One to two weeks, dependent on ambient temperature.

*Number per cluster.*—1 to 3 with single flowers most common.

FRUIT

Maturity when described: Firm ripe, Aug. 15, 2002.

Date of first picking: Aug. 12, 2002.

Date of last picking: Aug. 24, 2002.

Size: Uniform, large.

*Average diameter axially.*—3" [76.2 mm.].

*Average diameter across suture plane.*—3" [76.2 mm.].

*Typical weight.*—9.0 ounces [255 grams].

Form: Globose to slightly oblong, slightly compressed toward the suture.

*Longitudinal section form.*—Circular.

*Transverse section through diameter.*—Circular, slightly compressed toward the suture.

Suture: A sharp groove from the stem to the shoulder, becoming a shallow trough along the sides, deepening again toward the apex, and ending with a slight depression just beyond the pistil point.

Ventral surface: Rounded, lipped slightly stronger on one side, and evenly toward the apex.

Lips: Unequally along the side and evenly toward the apex.

Cavity: Flaring, circular, suture showing on one side, Light yellow [86. l.Y] stem markings typical.

*Depth.*—9/16" [14.3 mm.].

*Breadth.*—1 1/16" [27.0 mm.].

Base: Truncate.

Apex: Rounded and somewhat cuneate when viewed along the suture.

Pistil point: Both apical and oblique, very short, depressed within the suture.

Stem: Medium.

*Average length.*—3/8" [9.5 mm.].

*Average width.*—3/16" [4.8 mm.].

Skin:

*Thickness.*—Medium.

*Surface.*—Smooth.

*Tenacity.*—Tenacious to flesh.

*Astringency.*—Slightly astringent.

*Tendency to crack.*—None observed in dry season.

*Color.*—Dark red [16. d.R] streaking over a Strong reddish orange [35. s.rO] background with an occasional Light yellow [86. l.Y] area if sun protected and very slight Light orange yellow [70. l.OY] freckling on the sides toward the apex.

Flesh:

*Color.*—Brilliant yellow [83. brill.Y] with Deep red [13. deep R] streaking close to the stone.

*Surface of pit cavity.*—Dark red [16. d.R] fibers breaking when twisted from the stone.

*Amygdalin.*—Moderate.

*Juice.*—Abundant, rich.

*Texture.*—Very firm, crisp.

*Fibers.*—Abundant, fine.

*Ripens.*—Fairly even.

*Flavor.*—A tasty blend of acid and sugar averaging 13 brix.

*Aroma.*—Moderate.

*Eating quality.*—Very good.

STONE

Type: Clingstone.

Form: Oval.

Hilum: Narrow, oval.

Base: Straight.

Apex: Acute, with an average tip angle of 90 degrees and length of 1/8" [3.2 mm.].

Sides: Equal.

Surface: Irregularly furrowed near the apex and pitted toward the base.

Ridges: Jagged toward the base.

External stone color: Moderate reddish brown [43. m.rRr].

Pit wall color when cracked: Grayish brown [61. gy.Br].

Cavity surface color: Deep yellowish brown [75. deep yBr].

Average pit wall thickness: 1/4" [6.4 mm.].

Average width: 15/16" [23.8 mm.].

Average length: 1 9/16" [39.7 mm.].

Average breadth: 3/4" [19.1 mm.].

Tendency to split: None observed.

Kernel:

*Form.*—Oval.

*Skin color.*—Light yellow [86. l.Y] when freshly removed.

*Pellicle color.*—Dark grayish brown [62. d.gy.Br].

*Vein color.*—Grayish yellowish brown [80. gy.yBr].

*Taste.*—Sweet.

*Viable.*—Yes.

*Average width.*—9/16" [14.3 mm.].

*Average length.*—7/8" [22.2 mm.].

*Amygdalin.*—Scant.

USE

Market: Fresh market and long distance shipping.

Keeping quality: Good. Fruit quality observed to remain in good condition after 21 days in standard cold room at 36° Fahrenheit [2° Celsius].

Shipping quality: Good.

Resistance to insects: No unusual susceptibilities noted.

Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected seed parent, 'August Red' (U.S. Plant Pat. No. 6,363) nectarine, by producing nectarines that are nearly globose in shape, very firm in texture, clingstone in type, mostly red in skin color, and yellow with some red streaking in flesh color, but is distinguished therefrom by producing fruit that matures about two weeks earlier and that has a sweet kernel instead of bitter.

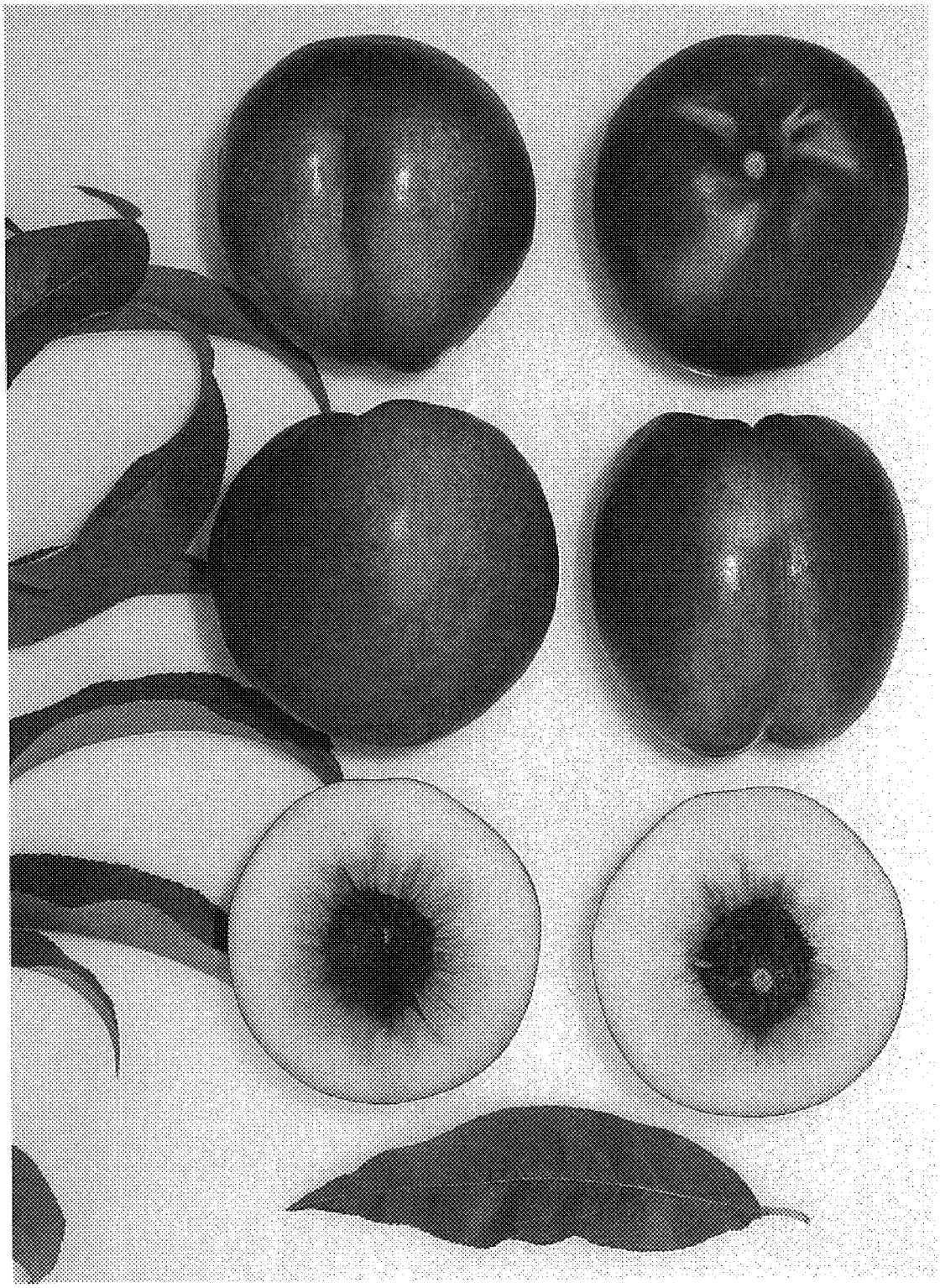

* * * * *